United States Patent
Hellgren et al.

(10) Patent No.: US 10,436,708 B2
(45) Date of Patent: Oct. 8, 2019

(54) METHOD FOR QUANTIFYING THE AMOUNT OF OPTICALLY INTERFERING GAS IMPURITIES

(71) Applicant: INFICON GmbH, Bad Ragaz (CH)

(72) Inventors: Johan Hellgren, Linkoping (SE); Henrik Vennerberg, Linkoping (SE); Fredrik Enquist, Linkoping (SE)

(73) Assignee: INFICON GmbH, Bad Ragaz (CH)

(*) Notice: Subject to any disclaimer, the term of this patent is extended or adjusted under 35 U.S.C. 154(b) by 0 days.

(21) Appl. No.: 16/076,729

(22) PCT Filed: Feb. 10, 2017

(86) PCT No.: PCT/EP2017/053012
§ 371 (c)(1),
(2) Date: Aug. 9, 2018

(87) PCT Pub. No.: WO2017/137565
PCT Pub. Date: Aug. 17, 2017

(65) Prior Publication Data
US 2019/0041317 A1    Feb. 7, 2019

(30) Foreign Application Priority Data
Feb. 11, 2016 (EP) .................................. 16155276

(51) Int. Cl.
*G01N 21/00*   (2006.01)
*G01N 21/27*   (2006.01)
(Continued)

(52) U.S. Cl.
CPC ....... *G01N 21/276* (2013.01); *G01N 21/3504* (2013.01); *G01N 21/37* (2013.01);
(Continued)

(58) Field of Classification Search
CPC ... G01N 21/276; G01N 21/3504; G01N 21/85
See application file for complete search history.

(56) References Cited

U.S. PATENT DOCUMENTS

| | | |
|---|---|---|
| 4,393,304 A | 7/1983 | Ishida et al. |
| 5,102,806 A | 4/1992 | Mikasa et al. |
| (Continued) | | |

FOREIGN PATENT DOCUMENTS

| | | |
|---|---|---|
| DE | 19911260 A1 | 9/2000 |
| EP | 1148337 A2 | 10/2001 |
| (Continued) | | |

*Primary Examiner* — Hugh Maupin
(74) *Attorney, Agent, or Firm* — The Webb Law Firm (57) ABSTRACT

Described is a method for quantifying the amount of optically interfering gas impurities in a gas detection system comprising a sample gas inlet, a reference gas inlet, a gas modulation valve, and an infrared absorption gas detector used for analysis of methane or natural gas, wherein the gas modulation valve alternatingly connects the sample gas inlet to the gas detector during a sample gas time period and the reference gas inlet to the gas detector during a reference gas time period. The method includes measuring an infrared absorption for at least two different sample gas concentrations in the gas detector achieved via respective different ratios from the sample gas time period and the reference gas time period, and comparing amplitudes of different measurement signals of the at least two different sample gas concentrations with calibration functions to assess an actual gas impurity concentration in the sampled gas.

10 Claims, 3 Drawing Sheets

(51) Int. Cl.
*G01N 21/3504* (2014.01)
*G01N 33/00* (2006.01)
*G01N 21/37* (2006.01)
*G01N 21/85* (2006.01)

(52) U.S. Cl.
CPC ......... *G01N 21/85* (2013.01); *G01N 33/0026* (2013.01); *G01N 2021/3545* (2013.01)

(56) References Cited

U.S. PATENT DOCUMENTS

| | | |
|---|---|---|
| 6,473,175 B1 | 10/2002 | Malczewski |
| 6,635,875 B1 | 10/2003 | Bley et al. |
| 7,030,381 B2 | 4/2006 | Kilian et al. |
| 7,063,667 B1 | 6/2006 | Ben-Oren et al. |
| 2010/0326169 A1* | 12/2010 | Grosse-Bley ......... G01M 3/202 73/31.05 |
| 2011/0077545 A1 | 3/2011 | Eichler |
| 2018/0313749 A1 | 11/2018 | Enquist et al. |

FOREIGN PATENT DOCUMENTS

| | | |
|---|---|---|
| EP | 3163290 A1 | 5/2017 |
| EP | 3163299 A1 | 5/2017 |
| EP | 3193166 A1 | 7/2017 |

\* cited by examiner

METHOD FOR QUANTIFYING THE AMOUNT OF OPTICALLY INTERFERING GAS IMPURITIES

CROSS-REFERENCE TO RELATED APPLICATIONS

This application is the United States national phase of International Application No. PCT/EP2017/053012 filed Feb. 10, 2017, and claims priority to European Patent Application No. 16155276.5 filed Feb. 11, 2016, the disclosures of which are hereby incorporated in their entirety by reference.

BACKGROUND OF THE INVENTION

Field of the Invention

The invention relates to a method for quantifying the amount of optically interfering impurities in a gas detection system comprising an infrared absorption gas detector, particularly a non dispersive infrared (NDIR) absorption detector used for methane and natural gas analysis. The result can be used to compensate for concentration prediction errors caused by the impurities present in the gas.

Description of Related Art

Regulations throughout the world require regular survey of gas networks to check for unknown leakage. The reason for this is primarily to protect the public from fires and explosions resulting from gas collecting in buildings and other confined spaces. The leak survey is typically carried out by moving a detector, sensitive to one of the main components of the gas, over the surface of the ground above the pipe carrying the gas.

The most common type of network gas is compressed natural gas (CNG) consisting mainly of methane with various amounts of nitrogen, carbon dioxide, ethane, other hydrocarbons and some other minor residuals. The non-methane gases are collectively called impurities in the following.

A second type of network gas is liquified petroleum gas (LPG) which contains mainly butane and propane.

A third type of gas is biogas (BG) which is currently emerging as a "cleaner" source of energy. This is yet on a very limited level and today seldom distributed in general gas networks.

The above three types of gases distributed in pipelines or vessels are denoted utility gas in the following.

If a utility gas signal is registered it can originate from two main sources: the gas installation under inspection or from biological decay processes. Examples of such biological sources are covered waste dumps, decomposing sewage, landfills etc. Gas originating from such sources is known by numerous names including marsh gas, soil gas, landfill gas and sewer gas. In the following, the term swamp gas is used as a common denominator for flammable gas sources of biological origin. In order to avoid unnecessary excavations on swamp gas signals it is desirable to be able to distinguish between real gas leaks from the pipe under survey and indications from swamp gas.

The most common method used to discriminate between utility gas and swamp gas is making an analysis of the components of the gas to determine the presence of ethane gas and/or heavier hydrocarbons such as propane and butane. Most natural gas sources contain 0.5-8% of ethane while swamp gas does not contain any significant amounts of ethane.

There are at present no commercially available gas sensors with a high enough selectivity between methane and ethane to make such an analysis possible in real time. The analysis is, therefore, typically carried out using a gas chromatograph (GC) separating the different components of the gas sample into pulses exiting the chromatograph column at different times. Due to this time separation of the different components, the analysis is possible even with a non-selective sensor.

There are some ethane specific detectors on the market employing gas chromatography, cryogenic separation or advanced optical techniques. These instruments have reaction times in the order of several minutes or more.

Checking the integrity of utility gas pipes, typically, gas detectors with very high sensitivity are needed capable of picking up gas concentrations of a few ppm or less when moving a detector along the ground surface above a buried pipe. In the same application it is also necessary to have a detector that can quantify very high concentrations in the region from 1 to 100% of gas.

Achieving this wide range of detection with sufficient selectivity and accuracy normally requires several sensing devices or a combination of several detection technologies.

A typical type of sensor is an infrared gas absorption detector.

Infrared gas analyzers detect infrared radiation passing through a gas sample. Typically, an IR gas analyzer comprises an infrared source, a measurement section, such as a cuvette having a gas inlet and a gas outlet and an infrared sensor. The infrared source emits an IR radiation into and through the measurement section where it passes through the gas sample contained therein. The infrared sensor receives and senses the IR radiation passing through the gas sample. A typical infrared sensor often used in this type of detector is a non-dispersive infrared absorption detector (NDIR sensor). NDIR sensors measure the amount of infrared radiation in one or several wavelength ranges in the radiation passed through the gas to be analyzed. The selectivity of an NDIR sensor is determined by selecting the appropriate wavelength ranges to fit specific absorption lines of the respective gas to be measured. The measurement principle is based on the fact that specific gas components absorb infrared radiation. The absorption ranges are to be detected by the infrared gas analyzer.

The infrared sensor transduces the magnitude of variations in incoming IR radiation energy into an electrical signal. Some IR sensors employ piezo materials and are known as pyroelectric sensors. The piezo material absorbs incoming radiation causing a temperature shift which in turn induces a temporary electrical potential across the material that can be used as a measurement of the change in incoming radiation intensity.

Detection of low target gas concentrations in a gas sample in the range of parts per million (ppm) requires a long optical path, i.e. a long path in which the infrared radiation can interact with the molecules in the gas. Using affordable radiation sources, optical filters and infrared radiation detectors results in a given optical path length in the order of 50-150 mm to achieve a sensitivity of 1-10 ppm for methane. An optical path longer than 150 mm typically does not increase the performance further due to reflection losses in the gas tube carrying the gas and forming the cuvette of the infrared gas detector.

The reason for "long optical paths" to be used in the gas detector is to get a signal variation between clean air and the low concentration sample that is significantly larger than the noise in the system. Noise sources are mainly on the detector side including the detector itself and circuitry used to amplify and convert the signal to a manageable digital or analog signal.

The absorption in the gas follows Beer's Law which can be written as follows for the light intensity transmitted through an optical path (assuming non-divergent light):

$$I = I_0 \times e^{-\varepsilon L c}$$

where:
I=Intensity of light after passing through length L of gas sample.
$I_0$=Intensity of light passing entering gas sample optical path.
ε=Molar absorptivity (depending on gas type)
L=Length of optical path.
c=Concentration of gas absorbing the light.

This means that for a given length Δx there will be a fixed relative attenuation of the signal. As can be seen the differential sensitivity decreases with concentration and length of the optical path. The optical path needs to be long to be optimized for low ppm sensitivity and it therefore becomes very difficult to see the difference between for example 90% and 95% of the target gas.

An optical path being so long that this "saturation" phenomenon occurs is referred to as a "long optical path". In atmosphere content measurements it is referred to as a "thick atmosphere".

Another consequence of this behavior is that low concentrations of certain impurities in the methane can result in the natural gas being highly overestimated. This is the case for the ethane and other hydrocarbons typically seen in natural gas. An impurity causing this effect is called an interfering impurity or optically interfering impurity in the following.

Figure 1:
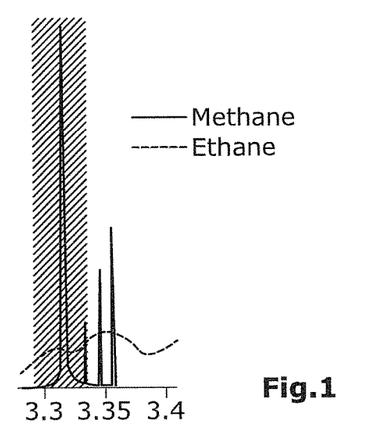
FIG. 1 is a graph illustrating the overlap of methane and ethane absorption used for the detection of methane, further to non-limiting embodiments or aspects of the invention.
Figure 2:
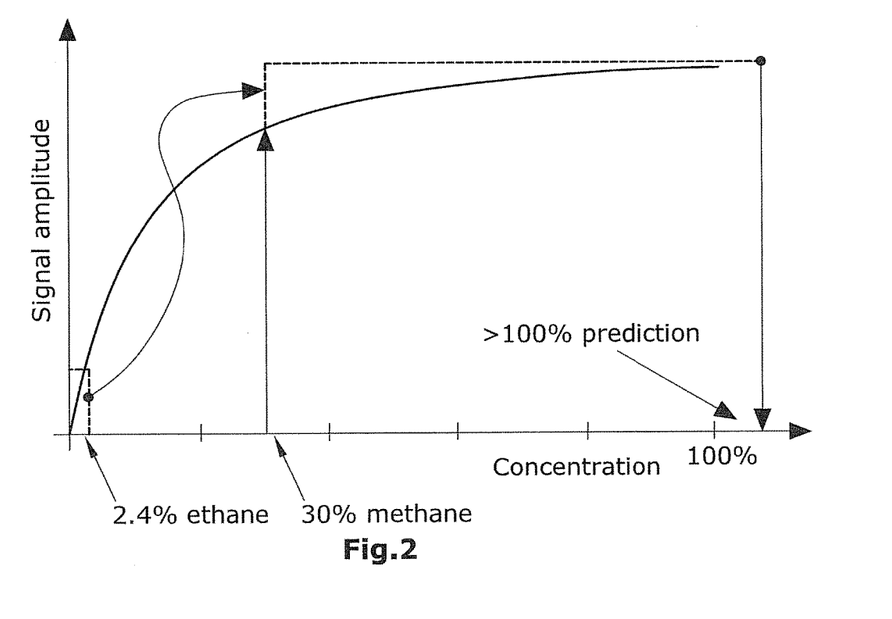
FIG. 2 is a graph illustrating the relationship between signal amplitude and concentration, further to non-limiting embodiments or aspects of the invention.

The different hydrocarbons absorb infrared radiation of slightly different wavelengths than methane. Unfortunately, these absorption peaks or bands overlap more or less and it is to date not possible to make affordable optical filters that can selectively filter out wavelengths that are completely specific for a certain hydrocarbon molecule. FIG. 1 shows a simplified graph showing the overlap of methane and ethane absorption in the 3.3 μm to 3.4 μm region often used for detection of methane.

The hatched area in FIG. 1 illustrates the bandwidth of the optical filter and the absorption in the optical path will be a function of the integrated area under the methane and ethane lines within the bandwidth of the filter width.

This gives a non-ideal selectivity for all concentrations which is not much of a problem for low concentrations as the absorption of the different components of the natural gas mix is close to linear for low concentrations.

The typical concentration of ethane in natural gas ranges from 0.5% to 8%. This means that for high gas concentrations the absorption by methane may be in the saturation while the ethane is absorbing in non-saturated conditions.

The part of the light that falls outside the wavelengths of the methane peak but within the band pass filter width and in this case inside the ethane absorption band will be attenuated by the ethane and so will therefore the total optical power passing the filter and detected by the IR sensor.

Knowing the actual gas mix in the pipe, it is, of course, possible to calibrate the system using that mix. In practice, this is seldom feasible.

It has already been established that it is not practical to use a fixed natural gas mixture to calibrate as the composition in the network varies unpredictably.

A method is known to improve the signal to noise of an IR detector by employing a modulation valve passing either a gas sample or an ambient reference sample trough the optical path tube (called cuvette in the following) in a cyclic manner. The reference sample is typically ambient air or a zero gas having no or very low concentration of the gases absorbing in the wavelength range analyzed.

Such a gas modulation valve and a respective gas modulation method are described in U.S. Pat. No. 7,030,381 B2, the contents of which are incorporated herein by reference. Gas detectors according to U.S. Pat. No. 7,030,381 B2 may comprise a sample gas inlet through which the gas to be detected (target gas) is sucked in, and a reference gas inlet through which gas from the surrounding atmosphere is sucked in as a reference gas. The gas modulation valve connects the sample gas inlet and the reference gas inlet to the inlet of a gas sensor, such as an infrared gas sensor. The infrared gas sensor may, for example, have a cuvette comprising the inlet and a respective outlet for the gas to be analyzed, an infrared light source and an infrared detector. The gas flow path from the gas modulation valve to the inlet of the gas sensor (cuvette) is alternatingly connected to the sample gas inlet and to the reference gas inlet by the gas modulation valve. The switching by the gas modulation valve between the sample gas inlet and the reference gas inlet preferably occurs in a periodical manner at a periodic frequency, as described in U.S. Pat. No. 7,030,381 B2.

A gas detection method employing gas modulation using a gas modulation valve switching between a reference gas inlet and a sample gas inlet is also described in European Patent Application No. 15192115.2, the contents of which are incorporated herein by reference.

The main purpose of U.S. Pat. No. 7,030,381 B2 is to filter out or compensate for an increased level of the target gas in the ambient atmosphere surrounding the gas detector by presenting an output signal representing the difference in concentration of target gas at the sampling point and in the ambient atmosphere. Another consequence of using the gas modulation is a strongly enhanced signal-to-noise ratio as the gas modulation modulates the actual parameter to analyze, namely the gas concentration. The signal is the difference between light transmitted through the gas and through the reference instead an absolute value of light intensity. Analyzing the detector signal at the gas modulation frequency strongly suppresses various noise signals with other frequencies.

According to a method described in European Patent Application No. 16151030.0, the entire content of which is incorporated herein by reference, the sample gas time period during which the gas modulation valve connects the sample gas inlet to the gas inlet of the infrared absorption gas analyzer is shorter than the reference gas time period during which the gas modulation valve connects the reference gas inlet to the gas inlet of the infrared gas analyzer. The alternating switching of the gas modulation valve between the reference gas inlet and the sample gas inlet results in a gas modulation at a gas modulation frequency. The gas modulation frequency affects the amount of sample gas in the infrared gas analyzer, i.e. in the measurement volume (cuvette) of the gas analyzer. The shorter the sample gas time period compared to the reference gas time period, the lower is the sample gas concentration and, thus, the concentration of possible target gas within the gas analyzer. The longer the sample gas time period as compared to the reference gas time period, the larger is the amount of sample gas and, thus, possible target gas within the gas analyzer.

SUMMARY OF THE INVENTION

It is an objective of the present innovation to provide a fast method for analyzing an impurity gas content, such as methane, in a natural gas or a methane rich gas sampled in the vicinity of utility gas installations to discriminate utility gas from swamp gas, such as ethane.

Another objective is to provide a method for compensating the concentration prediction of natural gas for the actual interfering impurity level in the gas sampled.

Moreover, it would be desirable to be able to compensate the concentration prediction of natural gas for a respective interfering gas impurity level in a sampled gas.

The subject matter of the invention is further described below.

In one non-limiting embodiment, the infrared absorption is measured for at least two different sample gas concentrations in the gas detector achieved via respective different ratios of sample gas time period vs. reference gas time period, wherein the gas amplitudes of the different measurement signals are compared with calibration functions or curves representing the signal amplitude versus the gas concentration of different amounts of interfering gas impurities in the sampled gas (methane or natural gas) in order to thereby assess the actual gas impurity concentration in the sampled gas.

In another non-limiting embodiment, the infrared absorption is measured for at least two different sample gas concentrations in the gas detector achieved via a first measurement at the gas modulation frequency at which the gas modulation valve switches between the sample gas inlet and the reference gas inlet and via at least a second measurement at at least the first even overtone of the gas modulation frequency, wherein the amplitudes of the different measurement signals are compared with calibration functions (curves) representing the signal amplitude versus the gas concentration of different amounts of interfering gas impurities in methane or natural gas in order to thereby assess the actual gas impurity concentration in the sampled gas.

The main object or the gas modulation is to provide a large contrast between the gas sample and the reference sample. The sampling frequency and pump capacity must therefore be chosen so that all the gas in the cuvette is replaced in each of the two phases of the modulation cycle. For optimized speed and pump capacity it is suitable that the duty cycle is 50% i.e. the reference gas time period and the sample gas time period are equally long.

To make full use of the gas modulation we should evaluate the signal at the gas modulation frequency. This is necessary to achieve the optimum sensitivity for small gas concentrations in the ppm level.

The optical saturation phenomenon at higher concentrations makes it hard to maintain a high enough accuracy in the prediction of high concentrations. Secondly it "amplifies" the signal from interfering impurities. As explained above, the absorption in the gas follows Beer's-Law meaning that for long paths there will be a saturation effect observed for high concentrations. This effect is illustrated in FIG. 3.

Figure 3:
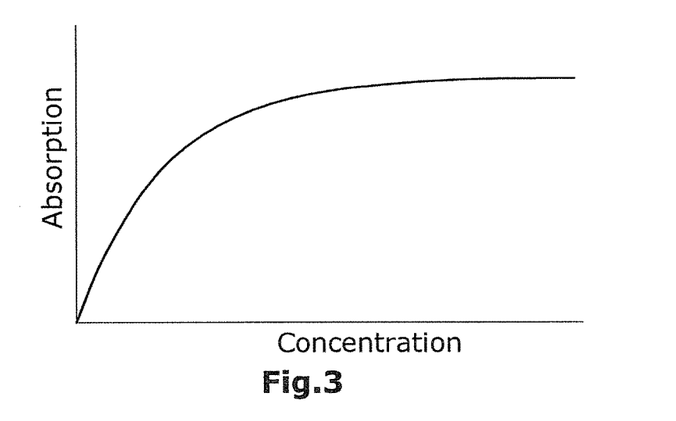
FIG. 3 is a graph illustrating the relationship between absorption and concentration, further to non-limiting embodiments or aspects of the invention.

As can be seen in FIG. 3, the differential sensitivity decreases with concentration. Using an optical path optimized for single parts per million (ppm) sensitivity, it becomes very difficult to see the difference between for example 90% and 95% natural gas.

The invention employs the gas modulation technique for reducing this problem.

DESCRIPTION OF THE INVENTION

The gas modulation valve is used to mix or dilute the sample gas with reference gas to enable analysis of different concentrations to calibrate the detector for the actual gas being analyzed. This can be achieved by time controlled dilution of the average sample gas concentration in the cuvette of the IR absorption detector. Alternatively, this can be achieved by analyzing the signal amplitude at overtones of the gas modulation frequency. In both cases, at least two points of the measurement signal (absorption versus time) must be fit to a pre-recorded set of calibration functions or sensitivity curves for a number of different impurity levels (most commonly ethane).

The time controlled dilution according one non-limiting embodiment is achieved by controlling the lengths of the periods of sample gas and reference gas injection into the cuvette respectively. In one implementation the basic steps could be:

purge the cuvette with reference gas,
fill a pre-determined portion (X %) of the cuvette with sample gas by switching the modulation device to inject sample gas for the time needed to fill X % of the cuvette,
record the IR absorption signal X % average sample concentration,
inject some more reference gas to decrease the sample gas filled portion of the cuvette to Y % Y<X,
record the IR absorption signal at Y % average sample concentration,
fit the two recorded signals to the appropriate transfer function or sensitivity curve to determine the interfering impurity concentration.

Modulation of the infrared source by switching the same on and off repeatedly at a lamp modulation frequency may be achieved to record the signals. A pyroelectric sensor can be used that only reacts to changes in incoming optical power. The lamp modulation frequency may preferably be lower than the gas modulation frequency. The measurement signal of the infrared gas analyzer may then be analyzed at a detection frequency corresponding to the lamp modulation frequency or being an integer multiple of the lamp modulation frequency. The measurement signal of the infrared gas analyzer may simultaneously also be analyzed at one or several other frequencies each being integer multiples of the lamp modulation frequency.

The gas modulation frequency should be an integer multiple of the lamp modulation frequency. In the above, an integer multiple may be the same frequency, twice the frequency, three times the frequency, and so on.

The overtone method according to another non-limiting embodiment requires no controlled dilution. Rather, the cuvette of the infrared absorption gas detector is filled twice during a full gas modulation cycle, such as by setting the pump speed accordingly. Thereby, the average gas concentration in the IR absorption gas detector will vary in a triangular fashion as illustrated by the solid line in FIG. 4.

Figure 4:
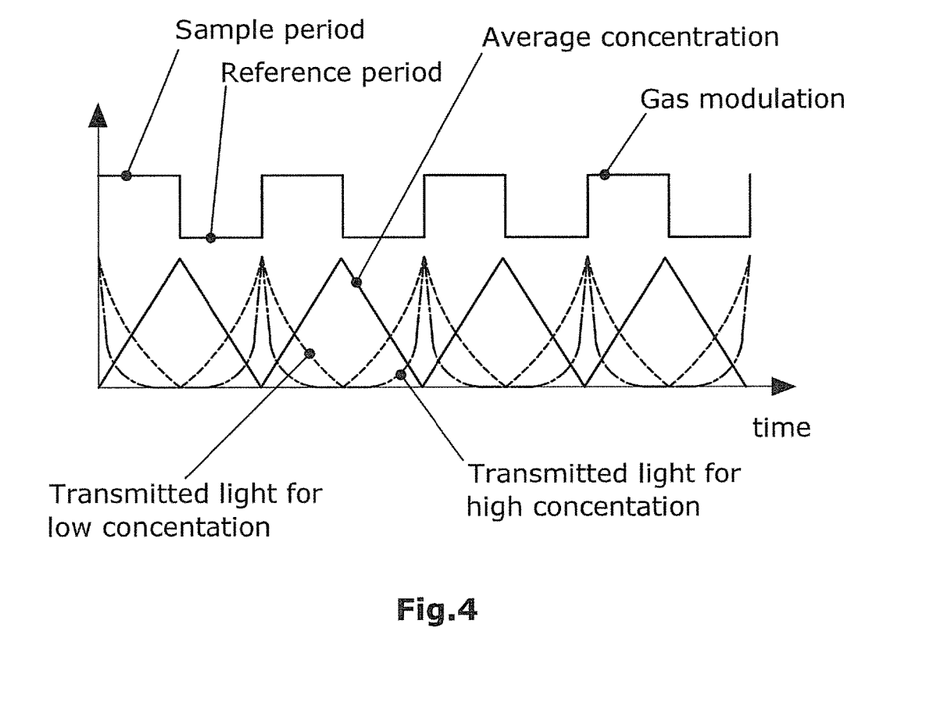
FIG. 4 is a graph illustrating the relationship of average concentration, gas modulation, and transmitted light over time, further to non-limiting embodiments or aspects of the invention.

Due to the Beer's-Law the transmitted light intensity (dot-dashed line in FIG. 4) will deviate significantly from the concentration wave form if the gas concentration is high whereas it will be more like the triangular concentration wave if the gas concentration is low (dashed line in FIG. 4). It should be noted that the amplitude of the two concentrations has been drawn equal for clarity. The amplitude of the low concentration signal is, of course, lower in reality.

Both the amplitude and the shape of the signal therefore hold information about the concentration.

The signal magnitude at any given moment in time is related to the average concentration in the cuvette at that specific time. This makes it possible to retrieve information about the signal achieved at different concentrations from one and the same sample concentration, in real time.

Using this method it is possible to simultaneously generate two or more calibration points or parameters representing the signal from a wide range of concentrations.

The calculated points or parameters are subsequently fitted to a pre-recorded set of transfer functions for different ethane content levels.

It is thus also possible to determine the ethane content and thereby compensate the signal to achieve a more correct total natural gas concentration prediction.

One way of retrieving this information is to analyze the amplitudes of the modulation frequency and one or several of the overtones of the same.

The necessary signal versus concentration curves can be established for a specific instrument in a factory test or during a yearly calibration, or if individual variations are within tolerance it would be possible to use a universal model specific set of curves and possibly a single known calibration mixture for regular calibration of the instrument. This calibration is not to be interpreted as the calibration for the unknown interfering impurity concentration in the gas sampled in the application.

In order to execute the method of the invention, the sample inlet is moved to a position where the detector signals that the gas concentration is suitable and stable, or the sample inlet is put in a high enough concentration and the gas detector creates the at least two needed concentration measurements by using the gas modulation to create suitable volume partitioning. It is advantageous if the detector automatically samples the signal and fits the result to the appropriate calibration curve. Moreover it is desirable that the detector presents the estimated ethane concentration to the user, for example on a display of the device. This procedure is then on the test side and requires only a few seconds after a reasonable gas concentration has been achieved. Typical total time is less than 15 seconds. The method of the invention applies to any limited contaminate (gas impurity) that absorbs radiation passing through the optical band pass filter, i.e. to any gas impurity having an absorption wavelength in the range of the analyzed absorption wavelength range of the gas sample.

Figure 5:
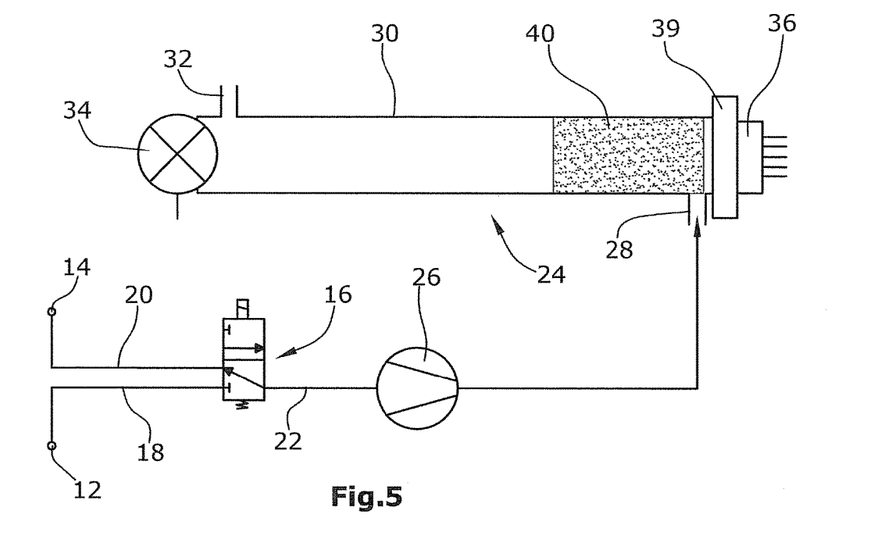
FIG. 5 is a schematic diagram of a system and method for quantifying the amount of optically interfering gas impurities, according to non-limiting embodiments or aspects of the invention.

In the following an embodiment of the invention is discussed with regard to FIG. 5.

A sample gas inlet 12 and a reference gas inlet 14 are connected to a gas modulation valve 16 via respective sample and reference gas conduits 18, 20. The gas modulation valve 16 alternatingly connects the sample gas conduit 18 and the reference gas conduit 20 to the gas flow path 22 connecting the gas modulation valve 16 and the gas detector 24. The gas detector 24 is a non-dispersive infrared (NDIR) sensor comprising an absorption cuvette 30. The gas flow path 22 contains a sample vacuum pump 26 located between the gas modulation valve 16 and the gas detector 24. The sample gas inlet 12 and the reference gas inlet 14 may be part of a handheld gas detector probe. This concept is described in U.S. Pat. No. 7,030,381 B2 and in European Patent Applications No. 15192135.0 and 15192115.2, the contents of which are incorporated herein by reference.

Accordingly, the gas modulation valve 16 switches between the reference gas conduit 18 originating from the reference gas inlet 12 and the sample gas conduit 20 originating from the sample gas inlet 12. The gas modulation valve 16 connects either of the conduits 18, 20 with the gas flow path (main gas conduit) 22. The gas to be analyzed is conveyed through the gas flow path 22 to the infrared gas detector 24.

The absorption cuvette 30 of the gas analyzer 24 comprises an inlet 28 through which the gas which is pumped by the sample pump 26 is guided into the absorption cuvette 30. The gas exits the cuvette through an outlet 32. An infrared source 34 is located at one end of the cuvette 30. The infrared source 34 is separated from the volume of the cuvette 30 through which the gas passes by an optical window which is not shown in the Fig. At the opposite end of the cuvette 30, an optical filter 39 and an infrared sensor 36 are located and separated from the volume of the cuvette 30 through which the gas sample passes by a further optical window which is not shown in the Figs. The optical windows may be made of Si, Ge or $CaF_2$ and are transparent for the infrared radiation originating from the source 34. The windows thereby separate the infrared source 34, the sensor 36 and the optical filter 39 from the gas flow path through the cuvette 30.

The optical filter 39 is preferably a dichroic or interference filter restricting the wavelength range passing through the optical window and detected by the infrared sensor 36, to the characteristic wavelength of the gas to be detected (target gas), for example methane. In general, the filter 39 should restrict the wavelength range of the infrared radiation to a wavelength range comprising the wavelength of the target gas while not comprising wavelengths of other characteristic gases.

Infrared radiation originating from the infrared source 34 radiates through the optical window not shown in the Figs., into the volume of the cuvette 30 and through the gas sample passing through the cuvette 30, and then through the further optical window not shown in the Figs. and through the optical filter 39 before being received by the infrared sensor 36.

The sample vacuum pump 26 could alternatively be placed downstream of the gas analyzer 24, i.e. behind the outlet 32. The advantage of locating the pump 26 within the main gas conduit 22 between the gas inlet 12 and the gas analyzer 24 is that pressure drops in the cuvette 30 due to varying restrictions in sampling probes are avoided.

The gas modulation valve 16 is used to create a signal modulation for noise reduction and signal amplification. Thereby, the valve 16 takes gas from the sample gas inlet 12 at the actual point of interest, or from the reference gas inlet 14 from the background air in an alternating cycle. The output signal of the gas analyzer 24 is analyzed in relation to the switching frequency of the modulation valve 16 (gas modulation frequency) and sometimes also in relation to the phase in order to improve the sensitivity and to reduce background noise.

The gas detector 24 generates an electronic detector signal which is analyzed by an evaluation device which is not shown in the pictures. The evaluation device evaluating the measurement signal from the gas detector 24 and the control device controlling the gas modulation valve 16, may be a single component sharing a single processor, or separate components which might be electronically connected with each other to share and exchange data.

The evaluation device analyzes and evaluates the measurement signal from the sensor 36 at a detection frequency which might be controlled by the control device. The detection frequency is controlled by the control device depending on the gas modulation frequency. The detection frequency should be an integer multiple (once, twice, three times, . . . ) of the gas modulation frequency. At the detection frequency, the evaluation device captures the measurement signal from the sensor 36 in order to perform the gas analysis.

The control device also controls the lamp modulation frequency at which the infrared source 34 is switched on and off. The lamp modulation frequency should be lower than the gas modulation frequency of the switching valve 16 while the detection frequency corresponds to the lamp modulation frequency. This means that the electronic measurement signal from the sensor 36 is analyzed by the evaluation device at the lamp modulation frequency. The gas modulation frequency is also an integer multiple of (once, twice, etc.) the lamp modulation frequency.

According to the invention, the infrared absorption is measured for different ratios of sample gas time period vs. reference gas time period. A first measurement is taken at a ratio of sample gas time period versus reference gas time period which results in a high sample gas concentration within the cuvette. At least a second measurement is thereafter taken at a lower ratio of sample gas time period versus reference gas time period, resulting in a lower concentration of sample gas within the cuvette. The amplitudes of the different measurement signals are compared with calibration functions which are measured in advance of the actual measurement and stored in a memory of the evaluation device. Different calibration functions are stored in the evaluation device, which each represent the signal amplitude over the gas concentration of different concentrations of interfering gas impurities in a respective sample gas, such as natural gas or methane. Accordingly, the calibration functions are stored for different types of sample gases. The actual gas impurity concentration in the gas sample is assessed by electing the calibration function which has the closest or most similar signal amplitude as compared to the amplitude of the measurement signal. The gas impurity concentration of the elected calibration function is considered to be the actual gas impurity concentration of the measured gas sample.

The invention claimed is:

1. A method for quantifying an amount of optically interfering gas impurities of a sampled gas in a gas detection system comprising a sample gas inlet, a reference gas inlet, a gas modulation valve and an infrared absorption gas detector used for analysis of methane or natural gas, wherein the gas modulation valve alternatingly connects the sample gas inlet to the gas detector during a sample gas time period and the reference gas inlet to the gas detector during a reference gas time period, the method comprising:
   measuring an infrared absorption for at least two different sample gas concentrations in the gas detector achieved via respective different ratios from the sample gas time period and the reference gas time period; and
   comparing amplitudes of measurement signals of the at least two different sample gas concentrations with calibration functions representing signal amplitude versus gas concentration of different amounts of interfering gas impurities in methane or natural gas in order to thereby assess an actual gas impurity concentration in the sampled gas.

2. The method according to claim 1, wherein the infrared absorption is measured for more than two different sample gas concentrations and compared with the calibration functions in order to thereby assess the actual gas impurity concentration in the sampled gas.

3. The method according to claim 1, wherein the sampled gas is natural gas and an interfering impurity gas is ethane, another hydrocarbon heavier than air, or a mix of ethane and one or several other hydrocarbons heavier than air.

4. The method according to claim 1, wherein an infrared source of the gas detector is repeatedly switched on and off at a lamp modulation frequency that is lower than a gas modulation frequency, and wherein a measurement signal of the gas detector is analyzed at an integer multiple of the lamp modulation frequency.

5. The method according to claim 4, wherein the gas modulation frequency is an integer multiple of the lamp modulation frequency.

6. A method for quantifying the amount of optically interfering gas impurities of a sampled gas in a gas detection system comprising a sample gas inlet, a reference gas inlet, a gas modulation valve and an infrared absorption gas detector used for analysis of methane or natural gas, wherein the gas modulation valve alternatingly connects the sample gas inlet to the gas detector and the reference gas inlet to the gas detector at a gas modulation frequency, the method comprising:
   measuring an infrared absorption for at least two different sample gas concentrations in the gas detector achieved via a first measurement at the gas modulation frequency and via at least a second measurement at at least a first even overtone of the gas modulation frequency; and
   comparing amplitudes of measurement signals of the at least two different sample gas concentrations with calibration functions representing signal amplitude versus the gas concentration of different amounts of interfering gas impurities in methane or natural gas in order to thereby assess an actual gas impurity concentration in the sampled gas.

7. The method according to claim 6, wherein the infrared absorption is measured for more than two different sample gas concentrations and compared with the calibration functions in order to thereby assess the actual gas impurity concentration in the sampled gas.

8. The method according to claim 6, wherein the sampled gas is natural gas and an interfering impurity gas is ethane, another hydrocarbon heavier than air, or a mix of ethane and one or several other hydrocarbons heavier than air.

9. The method according to claim 6, wherein an infrared source of the gas detector is repeatedly switched on and off at a lamp modulation frequency that is lower than the gas modulation frequency, and wherein a measurement signal of the gas detector is analyzed at an integer multiple of the lamp modulation frequency.

10. The method according to claim 9, wherein the gas modulation frequency is an integer multiple of the lamp modulation frequency.

\* \* \* \* \*